United States Patent [19]
Akins, Jr. et al.

[11] Patent Number: 5,403,747
[45] Date of Patent: Apr. 4, 1995

[54] PROTEIN ASSAY USING MICROWAVE ENERGY

[75] Inventors: Robert E. Akins, Jr., Ashford, Conn.; Rocky S. Tuan, Chester Springs, Pa.

[73] Assignee: Thomas Jefferson University, Philadephia, Pa.

[21] Appl. No.: 207,896

[22] Filed: Mar. 7, 1994

Related U.S. Application Data

[63] Continuation of Ser. No. 861,616, Apr. 1, 1992, abandoned.

[51] Int. Cl.$^6$ ............................................. G01N 33/00
[52] U.S. Cl. ........................................ 436/86; 436/87; 436/88; 436/164
[58] Field of Search .................... 436/86, 87, 88, 164, 436/166; 422/21, 67, 63, 81, 100

[56] References Cited

U.S. PATENT DOCUMENTS

| | | | |
|---|---|---|---|
| 4,796,197 | 1/1989 | Lissot et al. | 422/67 |
| 4,948,975 | 8/1990 | Erwin | 250/361 C |

OTHER PUBLICATIONS

Lie Ken Jie et al. "The Use of a Microwave Oven in the Chemical Transformation of Long Chain Fatty Acids Esters." 1988 pp. 367–369.
Shui-Tein Chen et al. "Rapid Hydrolysis of Proteins and Peptides by Means of Microwave Technology and its Application to Amino Acid Analysis" 1987 pp. 572–576.
Giguere et al. "Application of Commercial Microwave Ovens to Organic Synthesis". 1986 pp. 4945–4948.
Gedye et al. "The Use of Microwave Ovens for Rapid Organic Sythesis" 1986 pp. 279–282.
Smith, et al., "Measurement of Protein Using Bicinchoninic Acid," *Analyt. Biochem.* 150:76–85 (1985).
Lowry, et al., "Protein Measurement with the Folin Phenol Reagent," *J. Biol. Chem.* 193:265–275 (1951).
"DC Protein Instruction Manual," Bio-Rad Laboratories, Richmond, Calif. (modified Lowry Assay).
Bradford, "A Rapid and Sensitive Method for the Quantitation of Microgram Quantities of Protein Utilizing the Principle of Protein Dye-Binding," *Analyt. Biochem.* 72:248–254 (1976).
Pierce, "BCA* Protein Assay Reagent Protocol and Information Manual 23220/23225," Pierce Chemical Co., Rockford, Ill. (1989).
Boon, et al., "Microwave Cookbook: The Art of Microscopic Visualization," Coulomb Press Leyden, Leiden, Netherlands (1989).

*Primary Examiner*—Donald E. Czaja
*Assistant Examiner*—Lien Tran
*Attorney, Agent, or Firm*—Woodcock Washburn Kurtz Mackiewicz & Norris

[57] ABSTRACT

A modification of the standard BCA protocol is provided that allows sensitive and reliable protein determinations in a matter of seconds utilizing a microwave oven to irradiate the samples. Methods of determining protein concentrations in a sample are disclosed comprising the steps of combining the sample with a BCA assay reagent in a sample container, placing the sample container into a microwave oven, irradiating the sample and measuring an absorbance value at 562 nm for the sample. Protein concentrations are then determined by comparing the absorbance value with a known value based on a calibration curve. In preferred embodiments, the calibration curve is generated by placing one or more standards in the microwave oven and irradiating the standards. Preferably, the step of irradiating the sample is carried out for a duration of less than about 60 seconds and most preferably, for a duration of about 20 seconds. The step of irradiating the sample most preferably comprises exposing the sample to microwave energy at a power level of between about 600 to about 650 watts at a frequency of about 2.45 GHz. In addition to the preferred embodiments using BCA assay reagents, it has been found that the incubation times of other protein assays, such as those based on the reaction with alkaline copper tartrate can also be significantly reduced by exposing the sample and the assay reagents to microwave irradiation.

12 Claims, 3 Drawing Sheets

PROTEIN ASSAY USING MICROWAVE ENERGY

The present invention relates to assays, and, more particularly relates to protein assays exhibiting shortened reaction times.

Portions of the research related to the present invention may have been supported by the United States through NIH Grant HD 15822. Accordingly, the United States may have certain limited rights to this invention.

This is a continuation of application Ser. No. 861,616, filed Apr. 1, 1992, now abandoned.

BACKGROUND OF THE INVENTION

Assays are known that take advantage of a sensitive and highly specific interaction between cuprous ($Cu^{+1}$) ions and the sodium salt of bicinchoninic acid (BCA) for the determination of protein concentrations in solution. See Smith, et al., "Measurement of Protein Using Bicinchoninic Acid", Analyt. Biochem. 150:76–85 (1985). At alkaline pH, proteins will reduce $Cu^{+2}$ to $Cu^{-1}$ in the presence of BCA, and this reaction forms product that absorbs light strongly at a wavelength of 562 nm. Since the production of $Cu^{+1}$ in the BCA assay is a function of protein concentration and incubation time, the protein content of unknown samples may be determined spectrophotometrically by comparing the sample absorption spectrum to that of known protein standards.

The ease with which an accurate BCA assay may be performed has made it preferable to and of greater general utility than the Biuret, Lowry or Bradford techniques reported in the prior art. See Lowry, et al. "Protein Measurement with the Folin Phenol Reagent",J. Biol. Chem. 193:265–275 (1951); "DC Protein Instruction Manual" Bio-Rad Laboratories, Richmond, Calif. (modified Lowry Assay); and Bradford, "A Rapid and Sensitive Method for the Quantitation of Microgram Quantities of Protein utilizing the Principle of Protein-Dye Binding", Analyt. Biochem. 72:248–254 (1976). This is especially true because of the low levels of interference caused by reagents commonly used in protein preparations, such as detergents, certain buffers and salts, and some reducing agents. See Pierce, "BCA* Protein Assay Reagent Protocol and Information Manual 23220/23225" Pierce Chemical Co., Rockford, Ill. (1989); Smith, et al. "Measurement of Protein Using Bicinchoninic Acid", Analyt. Biochem. 150:76–85 (1985).

A particular concern in the use of protein assays involves instances where such interfering compounds accumulate or partition differentially among samples. For example, some detergents may associate preferentially with membrane proteins compared to cytosolic proteins during chromatographic purification. In such situations, artificially high protein levels are determined for membrane proteins, even if appropriate corrections are made to account for the concentration of detergent in the buffer. The use of the BCA assay obviates this problem since many detergents do not interfere with the assay. See Smith, et al., referenced above.

Kits taking advantage of the above-described BCA reaction are available, for example, from Pierce Chemical Co. (Rockford, Ill.). Three standard variations of the BCA based protein assay are suggested by Pierce with incubation at either room temperature, 37 C., or 60 C. for a period of 30 to 120 minutes. See Pierce, "BCA* Protein Assay Reagent Protocol and Information Manual 23220/23225" Pierce Chemical Co., Rockford, Ill., (1989). In general, it is known that the sensitivity of standard BCA assays increases with elevated incubation temperature and/or longer incubation time, and the assay can be easily adjusted to the range of interest. However, the time required for BCA protein analysis diminishes its utility for a number of reasons. For example, a large number of samples cannot be examined in a reasonable amount of time, nor can samples be assayed from a system undergoing a changes on the order of minutes, since the assay results would always lag the changes in the system. Additionally, the presently available assays are disruptive in procedures that require protein determination at multiple intermediate steps. It would therefore be desirable to reduce the incubation time of protein assays without diminishing the sensitivity or accuracy of the assay. It is therefore an object of the present invention to provide methods and apparatus for determining protein concentration based on known assays that may be performed using incubation times on the order of seconds, while retaining appropriate levels of sensitivity, reliability, accuracy and resistance to interfering compounds. It is a further object of the present invention to provide assays that are easy to use and easily integrated into current laboratory practice.

SUMMARY OF THE INVENTION

In order to meet these and other objects, the present invention provides a modification of the standard BCA protocol that allows sensitive and reliable protein determinations in a matter of seconds utilizing a standard microwave oven to irradiate the samples. The methods and apparatus of the present invention are useful with other reactions, but for the reasons discussed above, the improved BCA protocol represents a preferred embodiment for the determination of protein.

The present invention thus provides methods of determining protein concentrations in a sample comprising the steps of combining the sample with a BCA assay reagent in a sample container, placing the sample container into a microwave oven, irradiating the sample and measuring an absorbance value at 562 nm for the sample. Protein concentrations are then determined by comparing the absorbance value with a known value based on a calibration curve. In preferred embodiments, the calibration curve is generated by placing one or more standards in the microwave oven and irradiating the standards. Preferably, the step of irradiating the sample is carried out for a duration of less than about 60 seconds and most preferably, for a duration of about 20 seconds. The step of irradiating the sample most preferably comprises exposing the sample to microwave energy at a power level of between about 600 to about 650 watts at a frequency of about 2.45 GHz. In general, the methods of the present invention may be adapted to analyze a plurality of samples. In addition to the preferred embodiments using BCA assay reagents, it has been found that the incubation times of other protein assays can also be significantly reduced by exposing the sample and the assay reagents to microwave irradiation. Thus, the present invention provides a general method of determining protein concentrations in a sample based upon the reaction of protein with an alkaline copper tartrate solution and Folin reagent. These methods comprise the steps of combining the sample with assay reagent in a sample container, placing the sample container into a microwave oven, irradiating the sample, and determining protein concentration, preferably by colorimetric analysis.

The present invention also discloses apparatus for conducting a BCA-based assay, comprising a microwave chamber for producing an homogeneous microwave field, a photodetector chamber for the detection of reaction product, and a controller. Most preferably, the apparatus also includes either a means for regulating the duration time of microwave exposure or a means for measuring the total amount of microwave exposure, or both. In a preferred embodiment, a microwave detector is provided for measuring the duration time of microwave exposure and providing a signal indicative of an intensity value of microwave energy in the microwave chamber. In certain automated embodiments, a flow system is connected to the controller and the controller controls the flow of one or more reagents from the flow system into a sample container.

DETAILED DESCRIPTION OF THE PREFERRED EMBODIMENTS

As noted above, three standard variations of the BCA-based protein assay use incubation at either room temperature, 37 C., or 60 C. for a period of 30 to 120 minutes. Since sensitivity is proportional to incubation temperature and time, the standard assay can be adjusted to the range of interest. The present invention provides a refinement to this protocol by taking advantage of the accelerated reaction rate that it has now been found to be produced by microwave irradiation. Preferably, the irradiation is carried out using a household microwave oven, such as the Whirlpool Model RJM7450 which has a capacity of 1.3 cubic feet and produces 650 watts of microwave energy at a wavelength of 2.45 GHz. However, other ovens or microwave heating chambers having different capacities, power levels and wavelengths may also be used with the present invention. For example, a 0.8 cubic foot General Electric microwave oven producing 600 watts (Model JEM18F001) was used to obtain the data shown in FIG. 1. As illustrated by the following Example and explained in further detail below, irradiating the samples in a household microwave oven allows the accurate, BCA-based determination of protein concentrations in a matter of seconds.

EXAMPLE I

Figure 1:
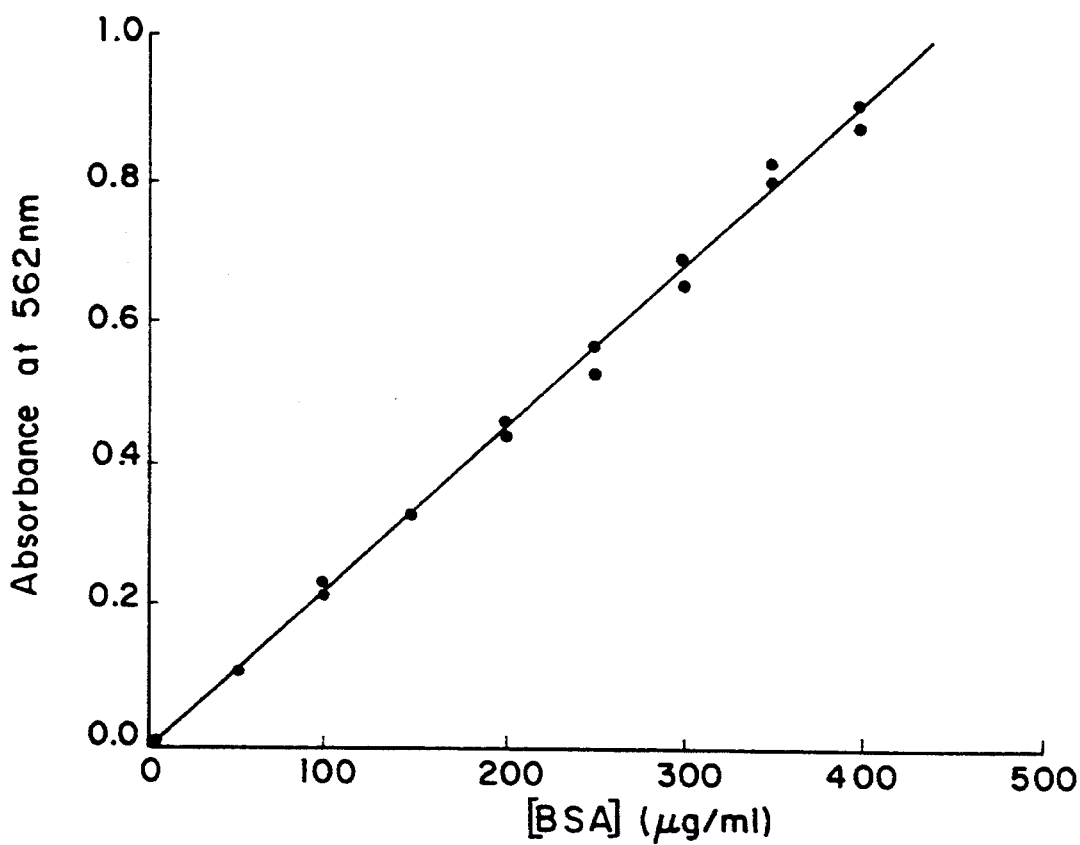
FIG. 1 illustrates a typical plot of absorbance versus bovine serum albumin concentration obtained using the BCA assay of the present invention.

A typical standard curve generated with the present invention using bovine serum albumin (BSA) dissolved in water is shown in FIG. 1. BSA is available, for example, from Sigma Chemical Co., St. Louis, Mo. Samples of BSA, in a volume of 100 $\mu$l, were prepared in triplicate and combined with 2 ml of BCA reagent in polystyrene Rohren tubes such as those available from Sarstedt Inc., Newtown, N.C. The tubes were placed in a plastic holding rack. It should be noted that metal holding racks should not be used in a an environment where they will be exposed to microwave radiation. A beaker containing 100 ml of room temperature water was also placed in the oven as an energy buffer to absorb some of the excess microwave energy. The provision of an energy buffer keeps the temperature of the samples from rising too rapidly and helps to maintain uniform exposure of the samples to microwave radiation. This technique is a known expedient in microwave heating techniques that have previously been applied as time-saving and efficiency-enhancing procedures. See, e.g., Boon, et al. "Microwave Cookbook: The Art of Microscopic Visualization" Coulomb Press Leyden, Leiden, Netherlands (1989). It appears, however, that while placing the test tube rack itself into a tray of water to better homogenize the water load and avoid any "hot spots" in the samples could be useful in some specific applications, in general, this step has been found to be unnecessary. The samples were placed in the center of the microwave oven and irradiated for 20 seconds on the highest setting. Absorbance values at 562 nm were measured within 5 minutes after irradiation and plotted against BSA concentration.

FIG. 1 shows a linear standard curve that would be suitable for the determination of protein concentration in unknown samples prepared during the same microwave run. Some variability in absorbance values obtained for a given BSA concentration was found under certain conditions, e.g., using different microwave ovens, changing the batch of BCA reagents, slightly lengthening or shortening irradiation times, or changing the size or starting temperature of the water load. This variability is easily compensated for by generating a BSA-based standard curve with each microwave determination as an internal control.

Figure 2:
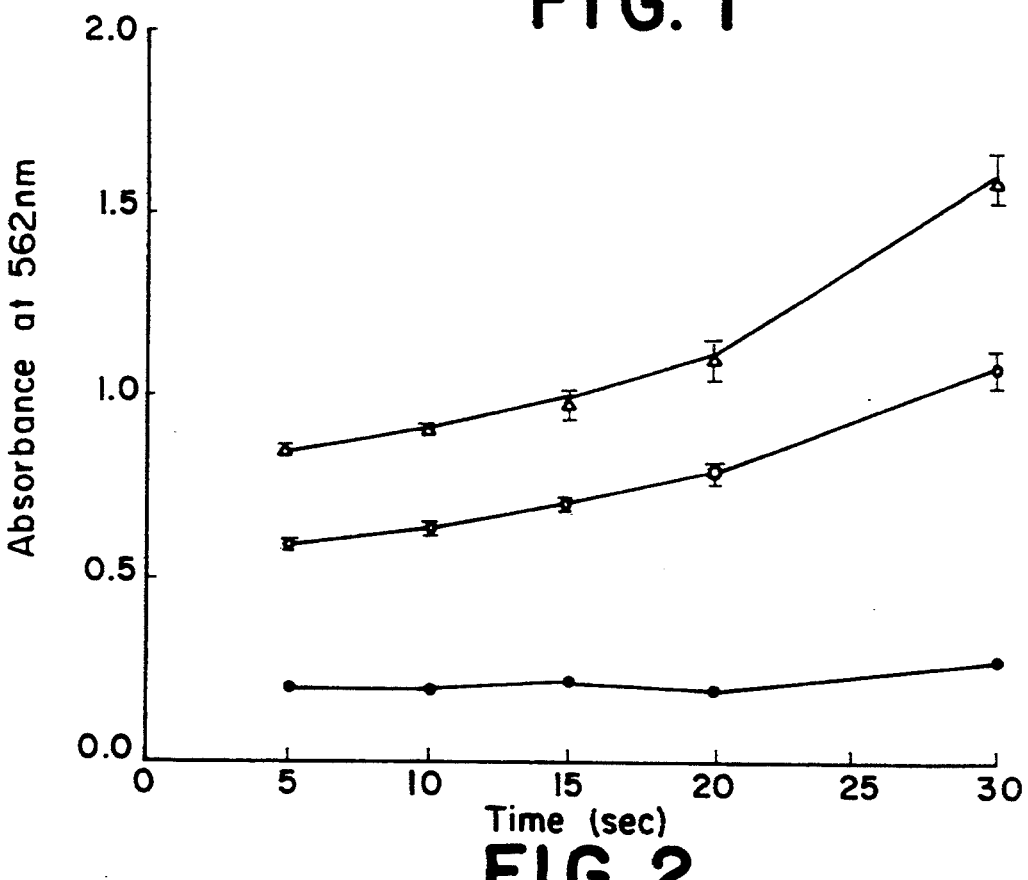
FIG. 2 illustrates the effect of increasing microwave irradiation time on the BCA assay of the present invention. Open triangles=1.0 mg/ml; open circles=0.8 mg/ml; and closed circles=0.2 mg/ml.

Using the microwave BCA procedure of the present invention, the effect of varying irradiation time on the reaction can also be determined. Referring now to FIG. 2, three concentrations of BSA (in water) were tested, and each time point was determined from a single irradiation trial, with the water load replaced before subsequent determinations. A single batch of BCA reagent was used throughout the experiment. Each value is the mean of triplicate samples ± standard deviation. Thus, FIG. 2 shows the rate of reaction for three different concentrations of BSA over 5-30 seconds of microwave exposure. It can be seen that absorbance values increased for each BSA concentration as a second order function of irradiation time. Curve fitting was done using Cricket Graph software (Cricket Software, Philadelphia, PA). The second order equations yielded a correlation coefficient =0.99 for each BSA concentration. Since a standard curve may be generated from BSA dilutions that are irradiated for specific times, in practice, the duration of microwave exposure can be selected to correspond to the sensitivity range desired, with longer times being more suitable for lower protein concentrations. The duration of 20 seconds chosen for the preferred embodiment of the microwave procedure described in Example I and for collecting other data discussed herein is more sensitive than a standard assay such as the Pierce assay discussed above, which is performed at room temperature.

Therefore, when further increases in sensitivity are desired, microwave exposure times are increased. As noted above, the duration of the irradiation is determined by using BSA test solutions in the range of protein concentrations expected until desirable absorbance values are obtained. By increasing microwave exposure time, it is thus possible to substantially increase assay sensitivity while still keeping the assay time below 60 seconds. The surprising ease with which sensitivity may be adjusted within extremely short time frames makes the microwave BCA the quickest, most flexible assay available for protein determinations.

As noted above, BCA assays generally do not suffer from inaccuracies caused by common laboratory reagents interfering with the assay. It has been reported in the literature, however, that certain compounds compromise the accuracy of BCA based assays. See Smith et al., "Measurement of Protein Using Bicinchoninic Acid," Analyt. Biochem. 150:76–85. (1985). Similar compromises are also likely to be true for the microwave BCA assay disclosed by the present invention. Moreover, because of the procedural variation, some originally non-interfering compounds could interfere with the microwave assay. For example, materials that absorb microwaves very efficiently might be particularly troubling since they would tend to shield samples from uniform exposure. In addition, compounds which are degraded or converted during the microwave procedure, as well as any that have altered interactions with other assay components, might also substantially affect the assay results. The interference of such materials can be predicted by considering the relative permittivities and dielectric characteristics of the samples being assayed. The determination or approximation of these microwave absorption characteristics are well known. However, interference, as with treatment duration, is most easily assessed empirically by directly determining the effect of a given additive on the accuracy and sensitivity of the assay.

Figure 3:
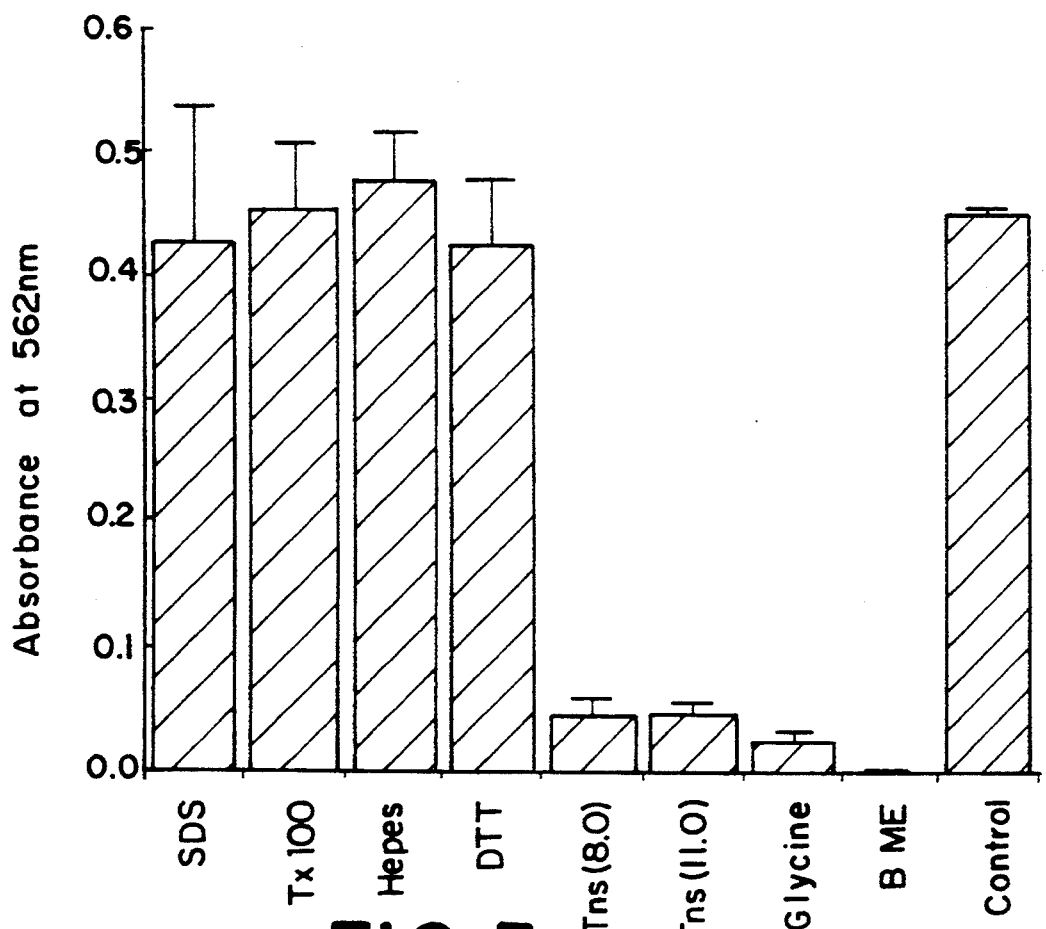
FIG. 3 is a bar graph illustrating the effect of common reagents on the BCA assay of the present invention.

The extent of the interference caused by selected compounds is shown in FIG. 3. These results are derived from a comparison of the absorbance values produced by 200 μg/ml BSA solutions containing various reagents during a 20 second microwave assay, as discussed above in Example I, to that produced by BSA in water alone. Stock preparations of BSA were prepared to give a final BSA concentration of 200 μg/ml in the presence of the reagents. The data presented are mean ± standard deviation (n=7). The treated samples were compared to a control (i.e., BSA in water only), and statistically significant differences are indicated with asterisks. By two-tailed Student's t-tests, SDS (1.0%), Triton X-100 (1.0%), Hepes buffer (0.1 M, pH 7.2), and dithiothreitol (DTT, 1 mM) did not interfere with the assay. It has been found, however, that Tris-HCl buffer (0.1 M, pH 8.0 or 11.0), glycine (1 M, pH 11.0), and β-mercaptoethanol (βME, 1.0%) all substantially affected the reaction. It has further been found, however, that for solution containing Tris-HCl or glycine, linear graphs of BSA concentration versus absorbance are obtained by including these compounds in the standard and all samples. On the other hand, βME interfered to such a large extent that the assay was not usable in its presence. As will be readily understood by those of ordinary skill, any compound added to the microwave BCA assay disclosed herein is easily checked for interference in a similar manner to assess its effects on both sensitivity and accuracy.

Thus, the present invention provides a microwave BCA protein assay protocol that most preferably comprises the steps of 1) combining samples and BSA standards with BCA assay reagent in polystyrene tubes 2); placing samples into a nonmetallic rack in the center of a microwave oven, along with a tray or beaker containing about 100 ml of room temperature water; 3) irradiating the samples, most preferably for about 20 seconds on the highest microwave setting; 4) measuring the absorbance at 562 nm for each sample; and 5) determining protein concentrations based on a BSA calibration curve. The microwave protein assay disclosed by the present invention is suitable for all situations where a BCA assay is presently used. The incubation time for a BCA-based protein assay using the methods known in the prior art is about 30–60 minutes, whereas a microwave BCA-based protein assay performed in accordance with the present invention requires incubation of less than 60 seconds. The ability to determine accurate protein concentrations in a relatively short time greatly facilitates routine assays and improves efficiency when protocols require protein determination at multiple intermediate steps.

The microwave assay discussed above in Example I has been used to generate chromatograms during protein purification and for general protein determinations, e.g., before electrophoretic analysis. The assay disclosed by the present invention consistently yields reliable results that are comparable to those obtained by the standard, 30 minute Pierce protocol discussed above. Moreover, the present invention is very easily adapted to any microwave oven and can be adjusted to cover a wide range of protein concentrations. Since the duration of the assay is so short relative to the incubation times found in the prior art, it is possible to run assays using several irradiation times and water loads to determine the specific conditions required by the particular microwave oven and samples being assayed. The microwave BCA assay of the present invention should therefore prove to be extremely useful in laboratories currently using BCA-based assays for protein determinations.

Another aspect of the present invention is the design of a microwave protein assay apparatus that advantageously uses the microwave enhanced assay of the present invention. The standard BCA assay disclosed in the Smith et al. article referenced above is a time-based assay which results in the continued production of product (purple color) over time. Therefore, as shown in FIG. 2, the duration of microwave exposure—which accelerates the rate of product formation—is directly related to the sensitivity of the assay. Thus, for a BCA-based assay conducted in accordance with the present invention, an apparatus must contain a means for regulating the time of microwave exposure or a means for measuring the total amount of microwave exposure, or both. In the absence of one of these two means, a standard curve must be generated each time on or more samples are assayed; with at least one of these means, it becomes possible to calibrate apparatus made in accordance with the present invention based on total microwave exposure (duration and field strength) so that standards need only be run periodically.

Figure 4:
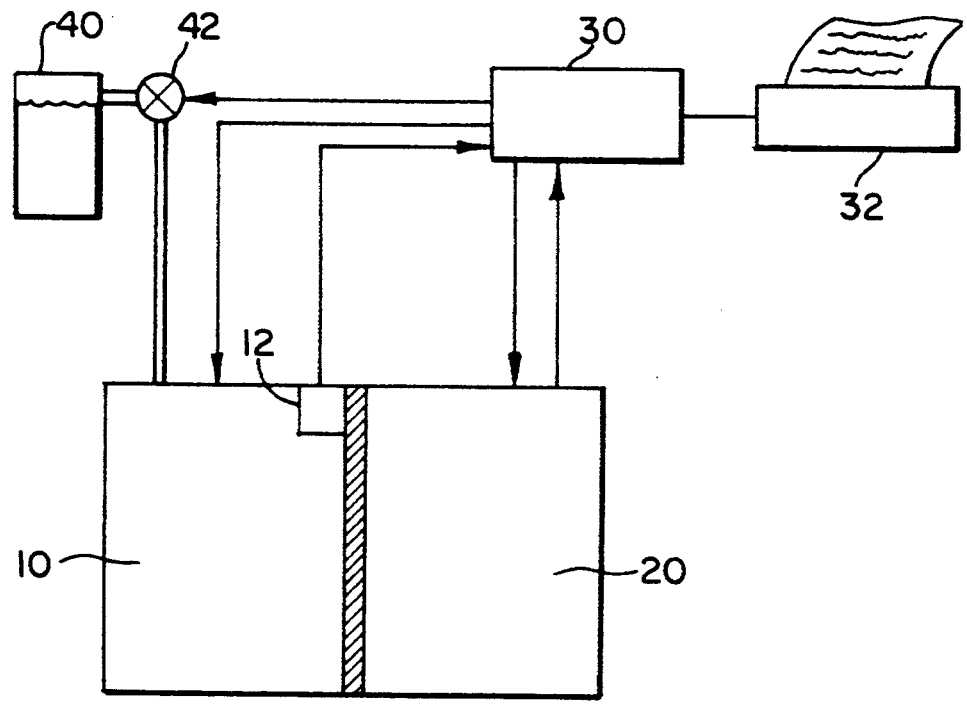
FIG. 4 is a schematic of a preferred embodiment of the apparatus of the present invention.

Referring now to FIG. 4, a schematic of an apparatus made in accordance with the present invention is shown. The apparatus preferably comprises a microwave chamber 10 that preferably produces an homogeneous microwave field, a photometer chamber 20 such as a spectrophotometer, colorimeter or fluorimeter for the detection of reaction product, and a controller 30. The specific dimensions and specifications of each of these components would be readily chosen by one of ordinary skill and are largely dependent on the maximum number of samples to be assayed. It should be noted, however, that a device made in accordance with the present invention is not necessarily comprised of three physically separate devices.

In a preferred embodiment, the microwave chamber 10 preferably operates at about 2.45 GHz, which is the standard frequency of commercially available microwave ovens. The production of relatively uniform microwave fields is well known to those of ordinary skill, as is that of the construction and operation of microwave detectors for this frequency. It should be noted that 2.45 GHz has been approved by the U.S. Federal Communications Commission for general use. In household microwave ovens, homogeneity of the electromagnetic field is obtained by scattering the microwave beam. Typically, microwave energy is transmitted via a waveguide to the top of the oven chamber and a fan with angled, reflective blades is spun in the path of the beam exiting from the waveguide, causing the energy to scatter. A relatively homogeneous field in three dimensions is completed by microwaves bouncing off the walls of the chamber in all directions. An alternative method for the production of an homogeneous microwave field utilizes geometrical optics and the placement of reflective surfaces in the light path. This method is used in many light sources for optical devices, but is not used in microwave devices due to alignment difficulties, spatial considerations and expense. Those of ordinary skill will appreciate that there are many variants to these methods of producing an homogeneous microwave field which may be applied in the design of apparatus made in accordance with the present invention. The principal concern, however, is that the field be substantially homogenous and that the chamber be designed so that all of the samples "see" the same microwave field.

Preferably, a microwave detector 12 should be included in the chamber 10. The detector 12 provides feedback of the intensity of microwave energy, which may vary over the lifetime of the microwave source, or due to power fluctuations or other causes. The detector 12 also provides information concerning the duration of microwave exposure, which is related to assay sensitivity in some cases.

In those embodiments wherein the photometer 20 is a spectrophotometer, the device is preferably comprised of a light source, a wavelength filter, and a detector connected to the controller 30 which converts transmittance readings into values which correspond to the optical density (OD) of the sample. The optical density value indicates concentration in each of the protein determination methods mentioned above; therefore, a microwave protein assay apparatus would preferably contain a spectrophotometric detector. The photometer 20 may be constructed to detect emissions from multiple samples from an assay in two different ways: in parallel, using an array of detectors to measure many samples at once, or by moving a plurality of samples past a single detector. The wavelength used for detection may be selected by the placement of individual filters in the detector light path or by the use of monochromators.

Commercially available multiwell microtiter plate readers (using filters) can measure and record the optical density of samples at a rate of approximately 50 samples per minute using a single detector. These readers are generally sold as microplate readers by companies such as Artek Systems Corp., Farmingdale, N.Y. and Bio-Rad Laboratories, Richmond, Calif. However, those of ordinary skill will understand that this rate of sample throughput is not limited and it may be possible to increase this rate further. The assay time for a single sample using either parallel or single detector configurations is estimated to be less than 30 seconds from the time the sample is placed in the device to the time a result is available. For large scale use, the number of assays that may be performed per minute is a function of the capacity of the microwave chamber 10 and the detector 12. Since, in theory, the microwave chamber 10 may be designed to hold as many samples as desired, the rate limiting step is detection, and as noted, rates for a single detector machine may be on the order of 50 samples per min. For a parallel machine, this rate may be multiplied by the number of detectors used. Thus, it can be seen that the present invention permits large numbers of samples to be performed in a matter of minutes if a plurality of detectors 12 are used in parallel.

The design of an apparatus for performing assays in accordance with the present invention may involve a separate microwave chamber 10 and a detection chamber containing the photometer 20, with a mechanical means to move samples from one compartment to the other, or it may involve a combined chamber where both irradiation and detection occur.

FIG. 4 also illustrates a computer-operated controller 30 for the monitoring of calibration and assay status, as well as the storage of specific assay parameters, results and, if desired, the control of reagent flow into each sample using an automated flow system 40 that preferably comprises a controlled valve 42 connected to the controller 30. Those of ordinary skill will be familiar with the construction and operation of automated flow systems and will further understand that the output of the flow system 40 illustrated may be directed to the samples after they are placed in the chamber, or, alternatively, may be directed to the samples when they are in another location, prior to their being transferred into the microwave chamber 10.

Thus, for example, in a preferred embodiment, a technician places a volume of sample into each well of a microtiter plate and places this plate into the microwave chamber 10. The addition of reagents would be controlled through valve 42 built into the apparatus so that each sample received the correct volume of reagent from a reservoir. The controller 30 would then turn on the homogeneous microwave field, monitor its intensity and duration using the detector 12 and turn off the field after a predetermined exposure. The controller 30 then activates the photometer 20 and reads the optical density of each sample, stores this value, converts the raw data into predetermined units, and displays data indicative of the results. Upon completion of an analysis cycle, the controller 30 preferably flushes the flow system 40 and, upon initiation of a new analysis cycle, the controller 30 would prime the flow system 40 and calibrate the apparatus for a range of protein concentrations and a given batch of reagents.

An additional component of the controller 30 is a hard copy output device 32 for the generation of reports concerning the status of the apparatus, results from particular assays and the like.

Figure 5:
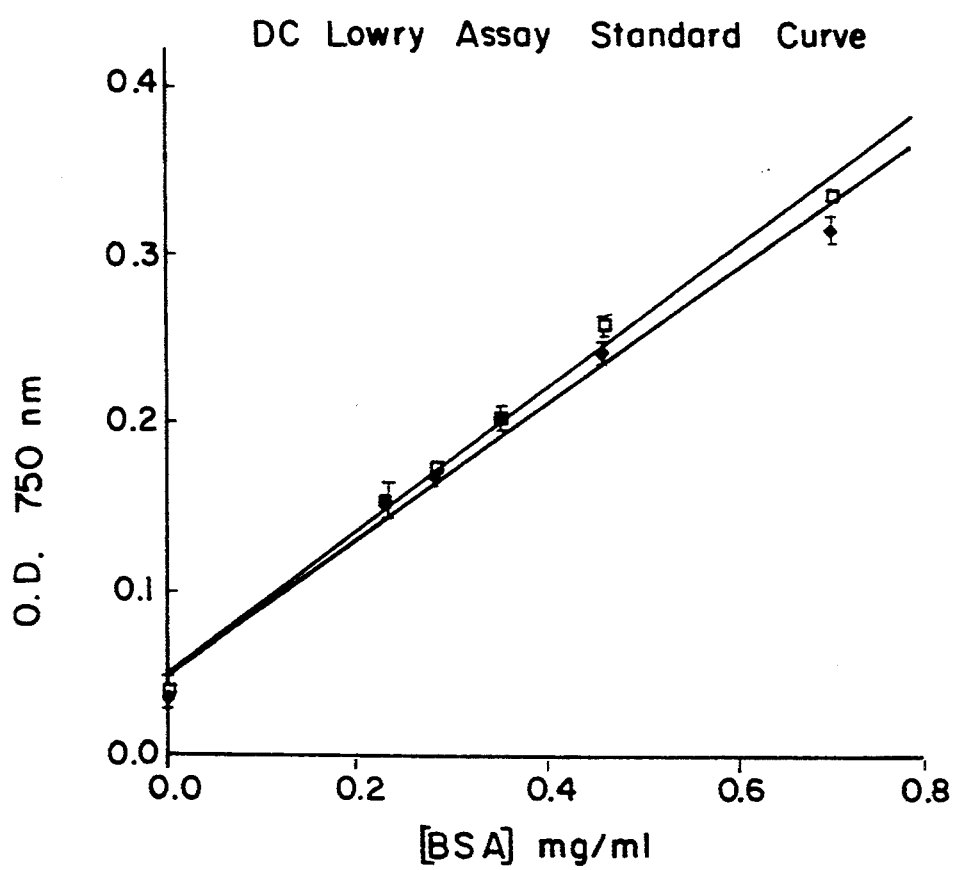
FIG. 5 is a plot similar to FIG. 1 showing the results of a microwave enhanced Lowry assay compared to a standard Lowry assay. Open squares=room temperature (RT) mean; closed squares=microwave ($\mu$w) mean.

The surprising results obtained using the present invention do not appear to correlate to other prior art assay techniques. As previously noted, the present invention permits sensitivity to be readily adjusted by varying the time of the microwave irradiation. As shown in FIG. 5, a comparison has been made of the results obtained using a prior art Lowry assay, described above, performed at room temperature with an incubation time of 15 minutes with a Lowry assay performed by exposing the sample and reagents to microwave energy in a manner similar to that described above in Example I, using irradiation time of 10 seconds. The Lowry assay is apparently an end point assay which results in a maximal level of product formed over time; therefore, as seen in FIG. 5, the duration of microwave exposure only accelerates the reaction as it progresses to completion and does not affect assay sensitivity. Thus, the measurement of protein concentrations using a microwave Lowry-based reaction may not require a built in calibration system. A Lowry-based apparatus would be calibrated periodically by running known standard proteins. The standard (non-microwave) incubation time for a Lowry based protein assay is 15–30 minutes; a microwave-Lowry based protein assay requires incubation of 10 seconds. Thus, it has been discovered that the incubation time may be significantly reduced. It should be noted, however, that extended irradiation times of more than 30 seconds of Lowry reaction mixtures containing BSA results in excessive heat production and the formation of a white precipitate of uncharacterized composition.

Thus, the present inventions also discloses methods for determining protein concentrations samples using a Lowry assay or other assays based upon the reaction of protein with an alkaline copper tartrate solution and Folin reagent. These embodiments of the present invention comprise steps of combining the sample with the appropriate assay reagents in a sample container, placing the sample container into a microwave oven and irradiating the sample. Protein concentration is then determined, preferably by colorimetric analysis, as is well known to those of ordinary skill.

Both the BCA and Lowry assays are extensions of the Biuret reaction described by Gornall et al. in the J.Biol.-Chem. 177:751 (1949). The BCA and Lowry assays allow for higher sensitivity over the Biuret reaction. The reason for the accelerated reactions upon exposure to microwave radiation is likely due to an increased rate of production of $Cu^{1+}$; therefore, a microwave apparatus like those described above may be useful in standard Biuret reactions for the reduction of incubation times. The standard (non-microwave) incubation time for a Biuret reaction based protein assay is 30 min; a microwave-Biuret reaction based protein assay would therefore theoretically require a shorter incubation time.

In conclusion, a microwave-based protein detection system may be designed to run any or all of the available protein determination reactions, most preferably a BCA assay but also either a Lowry assay or other assays based upon the Biuret reaction. The apparatus of the present invention may be designed to accommodate a large number of samples with high speed and represents an enhancement over any available system by virtue of the reduced incubation times necessary. The apparatus of the present invention may be designed to automatically carry out may of the steps necessary for the estimation of protein. This apparatus may be generally useful in assays where incubation of a mixture results in the production of a product with known transmittance properties (e.g. colorimetric enzyme assays, detection of sugars or other chemical compounds, etc.); adaptation of this apparatus to other assays may be done by simply controlling microwave exposure and the wavelength of detection.

Although certain embodiments of the present invention have been set forth with particularity, these examples are for the purpose of illustrating the invention and are not meant to be limiting. Accordingly, reference should be made to the appended claims in order to determine the scope of the present invention.

What is claimed is:

1. A method of determining protein concentrations in a sample comprising the steps of:
    combining the sample with a BCA assay reagent in a sample container;
    placing the sample container containing the sample and reagents into a microwave oven;
    irradiating the sample for about 20 seconds in the microwave oven, whereby a reaction between the sample and the reagent produces a product;
    measuring an absorbance value for the sample at a predetermined wavelength; and
    determining protein concentrations by comparing the absorbance value with a calibration curve representing absorbance as a function of concentration, created for the predetermined wavelength.

2. The method of claim 1, wherein the calibration curve is generated by placing one or more standards in the microwave oven and irradiating the standards.

3. The method of claim 1, wherein the step of placing the sample container into the microwave oven further comprises placing a quantity of water in the microwave oven.

4. The method of claim 1, wherein the predetermined wavelength is 562 nm.

5. The method of claim 1, wherein the step of irradiating the sample comprises exposing the sample to microwave energy at a power level of between about 600 to about 650 watts.

6. The method of claim 1 wherein the step of irradiating the sample comprises exposing the sample to microwave energy at a frequency of about 2.45 GHz.

7. The method of claim 1, wherein protein concentration is determined in a plurality of samples by combining the plurality of samples with a BCA assay reagent in a plurality of sample containers, placing the sample containers into the microwave oven, simultaneously irradiating the plurality of samples, measuring an absorbance value at 562 nm for each sample, and determining protein concentration in each sample by comparing the absorbance value with a calibration curve representing absorbance as a function of concentration.

8. A method for determining protein concentrations in a plurality of samples using apparatus for conducting a BCA-based assay that includes a microwave chamber, the method comprising the steps of:
    calibrating the apparatus for a range of protein concentrations and a given batch of reagents;
    placing a volume of a sample into each well of a multiwell plate to create the plurality of samples, wherein each well has a capacity sufficient to retain the volume of the sample and a predetermined volume of the reagents;

placing the multiwell plate into the microwave chamber;

adding the predetermined volumes of the reagents to each of the plurality of samples through a flow system comprising controlled valves;

activating a homogeneous microwave field within the microwave chamber;

monitoring an intensity and duration of the microwave field;

deactivating the microwave field after a predetermined exposure time period of about 20 seconds activating a detection system to determine an absorbance value for each one of the plurality of samples;

storing the absorbance value and converting the absorbance value to predetermined units indicative of the protein concentration in each sample; and displaying data indicative of the predetermined units.

9. The method of claim 8, further comprising the steps of:

flushing at the flow system;

priming the flow system; and recalibrating the apparatus for a range of protein concentrations and a given batch of reagents.

10. A method of determining protein concentrations in a sample based upon a reaction of protein with a reagent that initiates a Biuret reaction comprising the steps of:

combining the sample with assay reagent in a sample container;

placing the sample container into a microwave oven;

irradiating the sample for about 20 seconds; and determining protein concentration.

11. The method of claim 10 wherein the reagent comprises at least an alkaline copper tartrate solution and a Folin solution.

12. The method of claim 10 wherein the step of determining protein concentration comprises colorimetric analysis.

* * * * *